(12) United States Patent
Duncan (10) Patent No.: US 9,032,791 B2
(45) Date of Patent: May 19, 2015

(54) MEASURING HUMIDITY OR MOISTURE

(75) Inventor: Timothy Duncan, Grants Pass, OR (US)

(73) Assignee: Construction Technology Laboratories, Inc., Skokie, IL (US)

( * ) Notice: Subject to any disclaimer, the term of this patent is extended or adjusted under 35 U.S.C. 154(b) by 948 days.

(21) Appl. No.: 13/104,666

(22) Filed: May 10, 2011

(65) Prior Publication Data

US 2011/0277547 A1 Nov. 17, 2011

Related U.S. Application Data

(60) Provisional application No. 61/334,296, filed on May 13, 2010.

(51) Int. Cl.
   *G01N 19/00* (2006.01)
   *G01N 27/04* (2006.01)

(52) U.S. Cl.
   CPC ................................ *G01N 27/048* (2013.01)

(58) Field of Classification Search
   CPC ... G01N 27/223; G01N 27/048; G01N 25/56; G01N 33/383; G01N 19/10; H01R 39/64; H01R 35/04; H01R 13/2421; H01R 39/00
   USPC ............................ 73/29.01, 73, 29.05, 335.02
   See application file for complete search history.

(56) References Cited

U.S. PATENT DOCUMENTS

| | | | |
|---|---|---|---|
| 4,738,549 A * | 4/1988 | Plimpton | 374/208 |
| 6,305,944 B1 * | 10/2001 | Henry et al. | 439/22 |
| 6,793,146 B2 | 9/2004 | Cunkelman et al. | |
| 2001/0017053 A1 * | 8/2001 | Rynhart et al. | 73/73 |
| 2004/0140902 A1 * | 7/2004 | Staples | 340/602 |
| 2006/0272392 A1 | 12/2006 | Kanare | |
| 2009/0100926 A1 | 4/2009 | Kanare et al. | |

OTHER PUBLICATIONS

Office Action from the United States Patent & Trademark Office in U.S. Appl. No. 12/254,472, dated Mar. 16, 2011.

* cited by examiner

*Primary Examiner* — Daniel S Larkin
*Assistant Examiner* — Jamar Ray
(74) *Attorney, Agent, or Firm* — Klarquist Sparkman, LLP

(57) ABSTRACT

An apparatus for measuring humidity or moisture, such as in concrete, is described comprising a sensor module comprising a humidity or moisture sensor in electrical communication with a first set of terminals and a hand-held reader module comprising a controller in electrical communication with a second set of terminals that are mateable with the first set of terminals such that the hand-held reader module is electrically connectable to and electrically disconnectable from the sensor module. The hand-held reader module is configured to read data from the sensor in response to making electrical connection with the sensor module. One set of terminals can comprise plural connector pins and the other set of terminals can comprise plural landing pads, such that the plural connector pins and the plural landing pads make a same electrical connection regardless of the rotational orientation of the hand-held reader module relative to the sensor module.

20 Claims, 7 Drawing Sheets

MEASURING HUMIDITY OR MOISTURE

CROSS REFERENCE TO RELATED APPLICATION

This application claims the benefit of U.S. Provisional Application No. 61/334,296, filed May 13, 2010.

FIELD

This application relates to apparatuses and methods for measuring humidity or moisture in a subject material, such as concrete.

BACKGROUND

Relative humidity (RH) within concrete can be measured by performing in-situ testing at different depths within a concrete slab. An RH gradient exists within a slab of concrete that has its outer surface exposed; the RH increases as the depth into the slab increases. When the outer surface of the concrete slab is covered by a material that is close to impermeable, thereby preventing moisture from migrating out of the concrete surface, the RH gradient equalizes to an average RH throughout the slab that is about equal to the RH at 40% depth of an uncovered slab drying from the surface only (resting on a vapor retarder), or equal to the RH at 20% depth of an uncovered slab drying from both top and bottom.

A conventional practice for measuring RH in concrete includes forming a hole into a concrete slab at a certain depth, inserting a liner into the hole that will allow for sealing off the sidewalls of the concrete, placing of a seal at the top of the liner to seal off the internal environment, allowing for the equilibration of the RH of the internal environment, and then inserting a testing instrument into the liner to measure the RH. Most currently available instruments consist of a hole liner into which is inserted a probe that includes the sensor and a plastic enclosure. The probe is allowed to equilibrate, then taken out and moved to the next sleeve for the next measurement.

However, these currently available instruments result in undesirable problems relating to the thermal equilibrium of the sensing device and the concrete. Because RH is temperature dependent, it is therefore necessary that the RH sensing element be in thermal equilibrium with the environment being measured. With these currently available instruments, the probe portion that is inserted into the hole liner needs to come to thermal equilibrium with the concrete before an accurate measurement can be made. When a person handles the probe before insertion, heat is transferred into the probe, making the probe warmer and making the RH readings less accurate. Also, the ambient air is often times at a different temperature than the concrete environment to be measured, causing heat transfer across the probe. Even 1° F. of temperature change in the sensing element can cause inaccuracies in RH measurement of several percent.

In addition, some currently available instruments include a manual switch that is used by a person to take a measurement. The need to manually operate a switch can make the timing of the measurement long and uncertain.

SUMMARY

Disclosed herein are exemplary apparatuses and methods that make measuring humidity or moisture in a subject material, such as a concrete slab, quicker, simpler and more accurate, among other benefits.

In one aspect, apparatus for measuring humidity or moisture, such as in a material, such as concrete, includes a sensor module and a hand-held reader module. The sensor module includes a humidity or moisture sensor in electrical communication with a first set of terminals, such as a set of connector pins. The reader module includes a controller in electrical communication with a second set of terminals, such as a set of concentric landing pads, that are mateable with the first set of terminals such that the reader module is electrically connectable to and electrically disconnectable from the sensor module. The reader module is configured to read humidity or moisture data from the sensor in response to, such as in immediate response to, making electrical connection with the sensor module. The sensor module can be mounted within a sleeve that is embedded in the subject material and the reader module can be inserted into the sleeve to connect with the sensor module in order to take a reading.

The controller can have an interrupt line coupled to a first of the connector pins and a power or ground source coupled to at least a second of the connector pins. When the hand-held reader module is electrically connected to the sensor module, the first connector pin can be electrically connected to the second connector pin to create an interrupt signal to the controller and cause the controller to take a reading from the sensor.

The hand-held reader module, upon reading the sensor, can be configured to display a humidity or moisture value on a display for a predetermined period of time after the hand-held reader module is electrically disconnected from the sensor module or until the reader module is reconnected to the sensor module, such that a user can read and/or record the measurement value after the reader module is removed from the sensor module.

In some embodiments, the apparatus can be configured to wirelessly transmit information based on the humidity or moisture data to an external storage device, such as via Bluetooth™.

In another aspect, an apparatus for measuring humidity or moisture in a subject material includes a sensor module and a reader module. The sensor module includes a humidity or moisture sensor electrically connected a first electrical connector. The reader module includes a second electrical connector that is mateable with the first electrical connector to establish an electrical connection between the sensor module and the reader module. The reader module is electrically connectable to and electrically disconnectable from the sensor module. The second electrical connector is electrically connectable to the first electrical connector regardless of a rotational orientation of the reader module relative to the sensor module. One of the electrical connectors can be a set of spring-loaded connector pins while the other electrical connector can be a set of coplanar, concentric landing pads, such as on a printer circuit board, such that redundant pairs of the pins are arranged to contact the same landing pad when the reader module is connected to the sensor module.

Related methods and algorithms are also disclosed herein.

The foregoing and other objects, features, and advantages of the invention will become more apparent from the following detailed description, which proceeds with reference to the accompanying figures.

DETAILED DESCRIPTION

Described herein are exemplary embodiments of devices and related methods for measuring humidity or moisture. The following description is exemplary in nature and is not intended to limit the scope, applicability, or configuration of the invention in any way. Various changes to the described embodiments and methods may be made in the function and arrangement of the elements described herein without departing from the scope of the invention.

As used in this application, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed methods may be described in a particular, sequential order for convenient presentation, it should be understood that certain of the disclosed embodiments can encompass an order of operations other than the particular, sequential order disclosed. For example, operations described sequentially may in some embodiments be rearranged or performed concurrently. Further, descriptions and disclosures provided in association with one particular embodiment are not limited to that embodiment, and may be applied to other embodiments disclosed.

Embodiments described herein include features that enable humidity or moisture measurement, such as relative humidity (RH) measurement, in a subject material, such as concrete, without the disturbing effects of heat transfer from a user, ambient air, and/or the probe itself to the sensor, resulting in more accurate measurements. Exemplary subject materials can include water containing construction materials, such as concrete, cement, gypsum, wood and wood-based materials, and any other material having humidity, moisture, and/or other water content. While exemplary embodiments are shown in the accompanying figures and related descriptions that relate to measuring RH in concrete, it should be understood that these embodiment can be used with various subject materials other than or in addition to concrete, and that alternative embodiments can be configured to measure other characteristics of the subject material other than or in addition to RH, such as temperature and light sensitivity.

Figure 1:
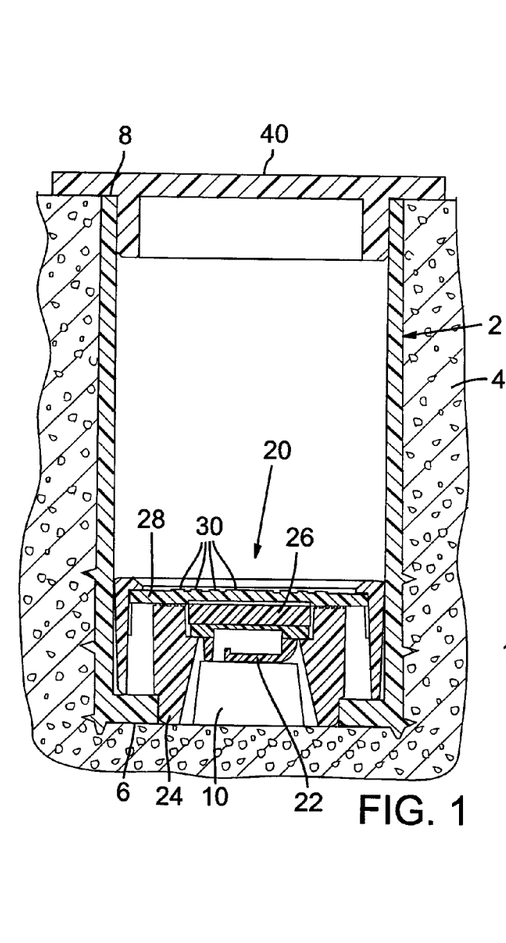
FIG. 1 is a cross-sectional view of an exemplary sleeve embedded in a material and having an exemplary sensor module mounted within the sleeve and a cover mounted over the sleeve.

FIG. 1 shows a sleeve 2 that is embedded into a hole in a portion of a subject material 4, such as concrete. The concrete hole can be formed by conventional means, such as drilling or pushing the sleeve 2 into wet concrete. The sleeve 2 can comprise a tube, such as a generally right-cylindrical tube, having a lower end 6 buried within the concrete and an open upper end 8 at the surface of the concrete. The lower end 6 of the sleeve 2 can comprise an opening 10 that exposes a portion of the concrete 4 below the sleeve to the hollow lumen within the sleeve. The sleeve 2 can also comprise one or more ribs or other irregular features 12 on its outer side surface that engage with the surrounding concrete 4. The ribs 12 can isolate and maintain an equilibrium environment of the effused moisture vapor underneath the sleeve as well as resist movement of the sleeve with respect to the concrete.

Figure 2:
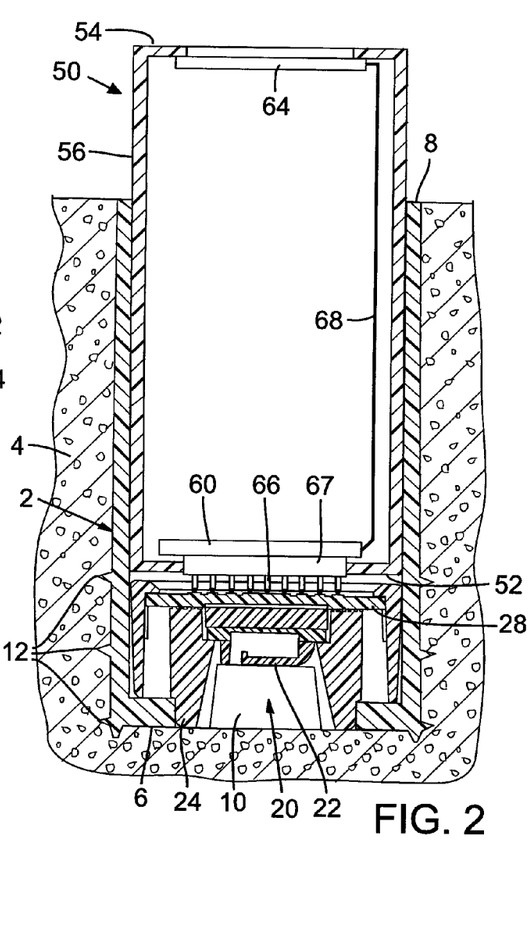
FIG. 2 is a cross-sectional view of the sleeve and sensor module of FIG. 1, wherein the cover is removed and an exemplary reader module is inserted within the sleeve and is in electrical contact with the sensor module.

A sensor module 20 can be insertable into and removable from the sleeve 2. The sensor module 20 is shown in FIGS. 1 and 2 in a functional position at the bottom of the sleeve 2, making a compression fit that acts to seal off the environment underneath that is to be measured. The sensor module 20 can comprise one or more sensors 22 for measuring the absolute humidity and/or temperature of the adjacent concrete that is exposed via the lower opening 10 of the sleeve 2.

Figures 3, 4:
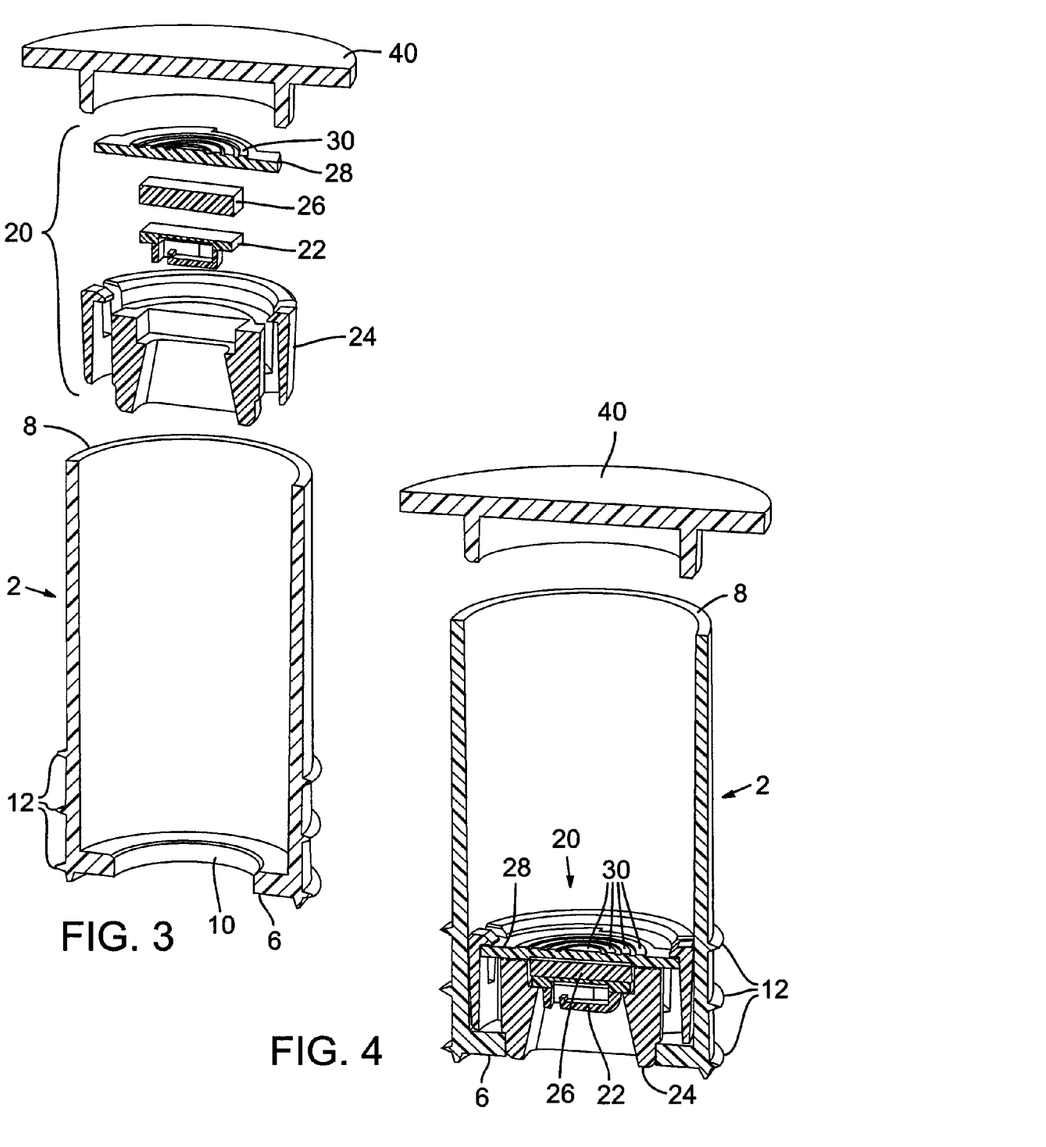
FIG. 3 is an exploded cross-sectional perspective view of the sleeve, sensor module and cover of FIG. 1.
FIG. 4 is cross-sectional perspective view showing the sleeve, sensor module and cover of FIG. 1 assembled together.

As shown in FIGS. 3 and 4, the sensor module 20 can further comprise a housing 24, a zebra strip or other equivalent electrical connector 26, and a set of electrical connection terminals, such as a printed circuit board (PCB) 28 comprising a plurality of concentric landing pads 30. The sensor 22 can be electrically coupled to the PCB 28 via the zebra strip 26. The sleeve 2 and the housing 24 can be comprised of polymeric material selected to have low thermal conductivity in order to reduce heat transfer to the sensor 22, with exemplary materials including acrylonitrile butadiene styrene (ABS) and high impact polystyrene (HIPS).

Figures 5, 6:
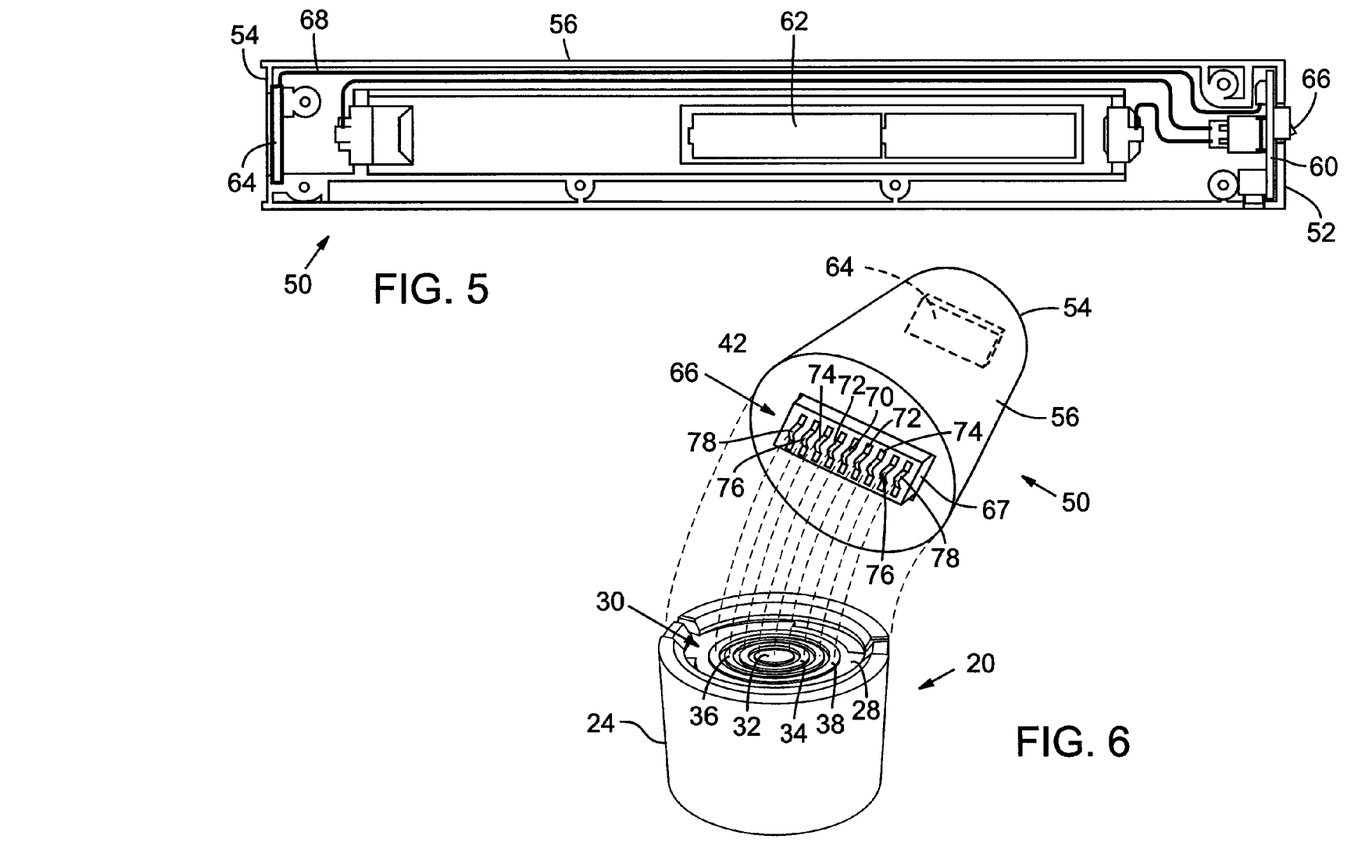
FIG. 5 is a plan view of the reader module of FIG. 2 with part of its housing removed.
FIG. 6 is a perspective view of the sensor module and reader module of FIG. 2, showing how an electrical connection is made between a set of connector pins on the reader module and a set of concentric landing pads on the sensor module.

As shown in FIG. 6, the landing pads 30 can comprise a disk-shaped central pad 32 and one or more annular rings, such as first ring 34, a second ring 36, and a third ring 38. The landing pads 30 can comprise electrically conductive material, such as gold-plated copper traces, and can be separated from one another by rings of insulating material, such a fiberglass or silicon-based material. Each of the landing pads 30 can comprise a planar upper contact surface and all of the planar upper contact surfaces can be coplanar. This geometry can be established by the use of the PCB 28, which fixes the relative positions of the landing pads 30. The PCB 28, being composed primarily of material having low thermal conductivity, can further help reduce heat transfer to the sensor 22.

The lower opening 10 of the sleeve 2 can be covered with a water-permeable material, such as Gortex®, that can prevent debris from entering the sleeve and interfering with the sensor 22, while allowing water vapor to pass. Such a cover material can be used, for example, when the sleeve 2 is to be inserted into wet concrete that could otherwise seep into the sleeve via the lower opening 10.

The open upper end 8 of the sleeve 2 can be enclosed with a cover 40, as shown in FIG. 1. The cover 40 can seal off the inner lumen of the sleeve 2 and protect the sensor module 20 exposure to the external atmosphere and reduce heat transfer between the ambient air and the sensor module 20. The cover 40 can be removed temporarily when an RH reading is to be taken from the sensor 22.

With the cover 40 removed, a reader module 50 can be inserted into the sleeve 2, as shown in FIG. 2, in order to perform an RH measurement. The reader module 50 can be configured such that an RH measurement is performed automatically in response to the reader module making contact with the sensor module 20 within the sleeve 2. In the embodiment shown, the reader module 50 comprises an elongated cylindrical housing having a lower end 52, an upper end 54, and a side wall 56. The configuration of the side wall 56 can be selected such that the lower end 52 of the reader module 50 fits closely within the inner lumen of the sleeve 2.

In an exemplary method of use, the sensor module 20 is left within the sleeve 2 with the cover 40 in place such that a thermal equilibrium is maintained between the sensor module 20, the sleeve 2, and the concrete 4. When an RH measurement is to be taken, a user can remove the cover 40 and insert the reader module 50 into the sleeve 2 until the lower end 52 contacts the sensor module 20. The reader module 50 can then automatically and quickly take absolute humidity and temperature readings from the sensor module 20 before any significant amount of heat is transferred from the reader module and/or the ambient air to the sensor module.

As shown in FIG. 5, the reader module 50 can comprise a controller 60 electrically coupled to a power source 62, a display 64, and a plurality of electrical terminals 66. The controller 60 can comprise a microcontroller and/or microprocessor configured to interact with the sensor 22 and the display 64, as described below. The power source 62 can comprise one or more batteries, for example, positioned within the reader housing. The display 64 can be positioned at the upper end 54 of the housing and can comprise a liquid crystal display (LCD), for example. The display 64 can be electrically coupled to the controller 60 via an electrical interconnect 68.

Figure 7:
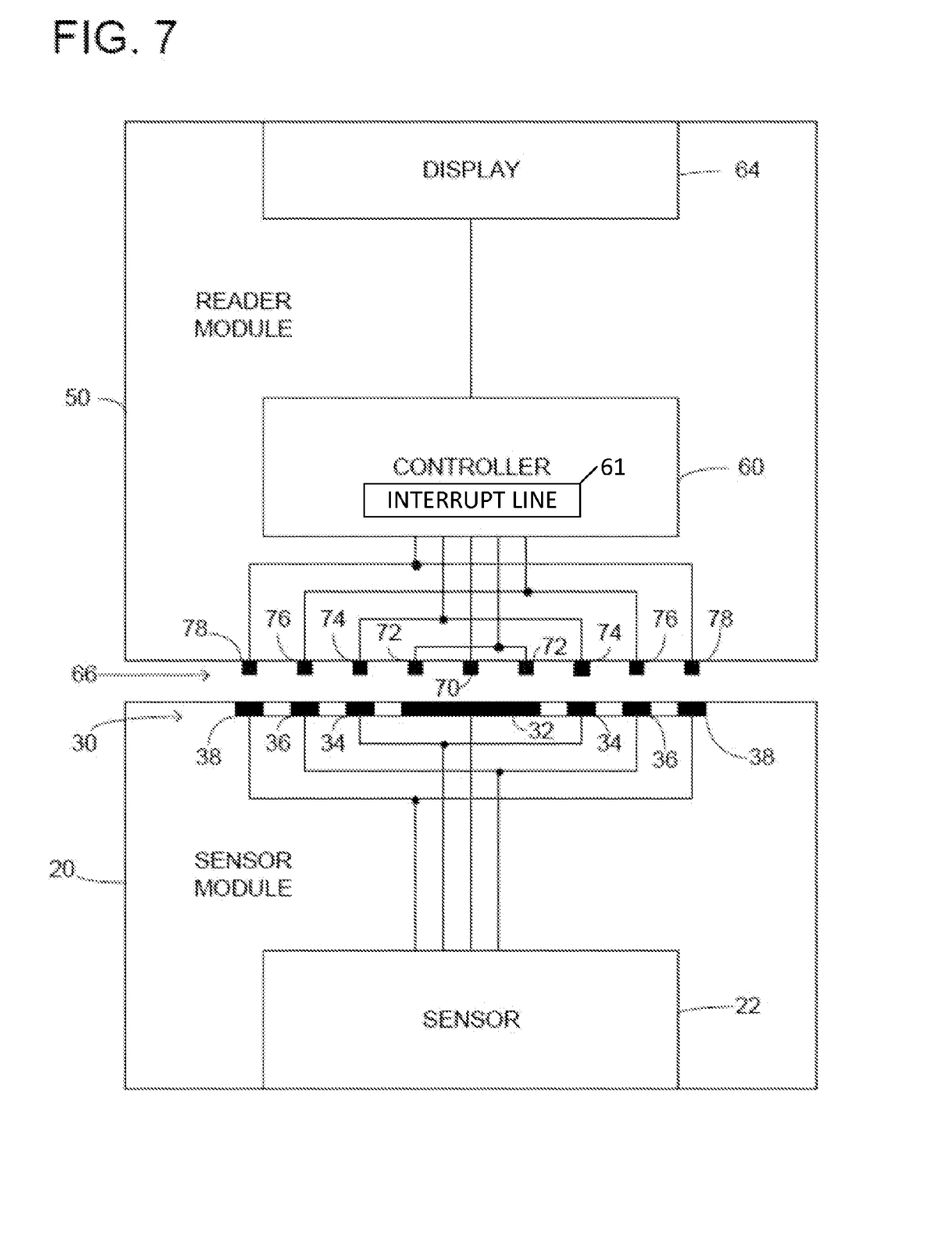
FIG. 7 is a schematic diagram showing elements of and electrical connections between the reader module and the sensor module of FIG. 2.

As shown in FIGS. 6 and 7, the plurality of electrical terminals 66 can be a plurality of connector pins, which can include a center pin 70 and one or more redundant pin pairs, such as a first pin pair 72, a second pin pair 74, a third pin pair 76 and a fourth pin pair 78. As shown in FIG. 7, each pair of redundant pins can be directly connected together and electrically coupled to a single line of the controller 60. As shown in FIG. 6, the plurality of connector pins 66 can included in a single board-to-board connector component 67 having spring loaded contacts and that is coupled to the controller 60.

When the reader module 50 is inserted within the sleeve 2, the pins 66 contact the landing pads 30 to electrically connect the controller 60 with the sensor 22. As shown in FIGS. 6 and 7, the center pin 70 and the first pin pair 72 contacts the central pad 32, the second pin pair 74 contacts the first ring 34, the third pin pair 76 contacts the second ring 36, and the fourth pin pair 78 contacts the third ring 38. As shown in FIG. 2, the contact between the pins 66 and the pads 30 can be the sole contact between the reader module 50 and sensor module 20. This pin-to-pad contact can comprise a minimal total surface area, which can minimize heat transfer between the reader module and the sensor module, making RH measurements more accurate.

In one exemplary embodiment, the center pin 70 can be electrically coupled to an interrupt line 61 of the controller 60, the first pin pair 72 can be electrically coupled to a ground line of the controller, the second pin pair 74 can be electrically coupled to a power line of the controller, the third pin pair 76 can be electrically coupled to a data line of the controller, and the fourth pin pair 78 can be electrically coupled to a clock line of the controller. In this embodiment, the central pad 32 can be electrically coupled to a ground line of the sensor 22, the first ring 34 can be electrically coupled to a power line of the sensor, the second ring 36 can be electrically coupled to a data line of the sensor, and the third ring 38 can be electrically coupled to a clock line of the sensor. In other embodiments, the order of the second, third and fourth pin pairs 74, 76, 78 and the first, second and third rings 34, 36, 38 with the respective controller lines and sensor lines can be rearranged in any manner so long as, when the reader module 50 is inserted into the sleeve 2, the power line of the controller is connected with the power line of the sensor, the data line of the controller is connected with the data line of the sensor, and the clock line of the controller is connected with the clock line of the sensor. In some embodiments, the center pin 70 can be electrically coupled to the ground line of the controller while the first pin pair 72 can be electrically coupled to the interrupt line of the controller.

The landing pads 30 can be concentric and symmetric about a center axis extending perpendicular to the coplanar upper surfaces of the landing pads. This symmetry can allow for an electrically equivalent connection to be formed between the connector pins 66 and the landing pads 30 when the reader module 50 is inserted into the sleeve 2, regardless of the rotational orientation, with respect the center axis, of the reader module relative to the sensor module. At any rotational orientation, the pins 66 of the reader module 50 land on the same landing pad 30 and make the same electrical connections. In other words, the electrical connection between the reader module 50 and the sensor module 20 can be rotation non-specific. Because of this rotation non-specific feature, when a user inserts the reader module 50 into the sleeve 2, the user can ignore the rotational orientation of the reader module, making the connection simpler, faster and less prone to connection errors. Because the connection can be made faster, a subsequent RH measurement can be made sooner, leaving less time for heat to transfer between the reader module and the sensor module, and rendering the RH measurement more accurate.

It should be understood that in alternative embodiments, the connector pins 66 can be swapped with the landing pads 30. For example, in some embodiments, the reader module 50 can comprise plural landing pads at a lower end thereof and the sensor module 20 can comprise a set of connector pins at an upper surface that are configured to mate with the landing pads when the reader module is inserted into the sleeve 2. This "reversed" arrangement can be functionally equivalent to the illustrated arrangement.

In some embodiments, the sensor 22 can be an SHT12-HWR-01 Humidity and Temperature Sensor from Sensirion Inc. The sensor can contain a CMOS based single chip multi-sensor providing a digital signal. The sensor can include a capacitive polymer sensing element for relative humidity measurement and a band-gap temperature sensor for temperature measurement. Both can be coupled to a 14-bit analog-to-digital converter and a serial interface circuit on the same chip. The sensor can communicate with the controller via a 2-wire serial interface. In some cases, the controller can download parameter values from the sensor can be used in a conversion formula to determine RH and temperature. The controller can read humidity data and temperature data in digital form from the sensor and use the conversion formula to determine RH and temperature values that can be displayed.

The controller 60 can comprise a conventional microcontroller/microprocessor unit that comprises typical hardware, such as an actual processor, memory (e.g., temporary memory and/or RAM), input/output connectors, etc., as well as embedded firmware and/or software for executing various functionalities.

Having described many structural features of the exemplary embodiments above, the following discussion describes exemplary related functional features and methods of use, with reference to FIGS. 8-11.

The controller 60 can have at least an active mode and a low-power, or standby, mode. In some embodiments, the controller 60 can have additional modes or sub-modes, such as a halt mode. In the active mode, the controller 60 can be configured to interact with the sensor 22 and/or the display to actively read data from the sensor and determine and/or display humidity and temperature values associated with the concrete. In the low-power, or standby, mode, the controller 60 can be configured to passively wait for an interrupt signal, or key change, and then switch to the active mode when the interrupt signal is received.

Figure 8:
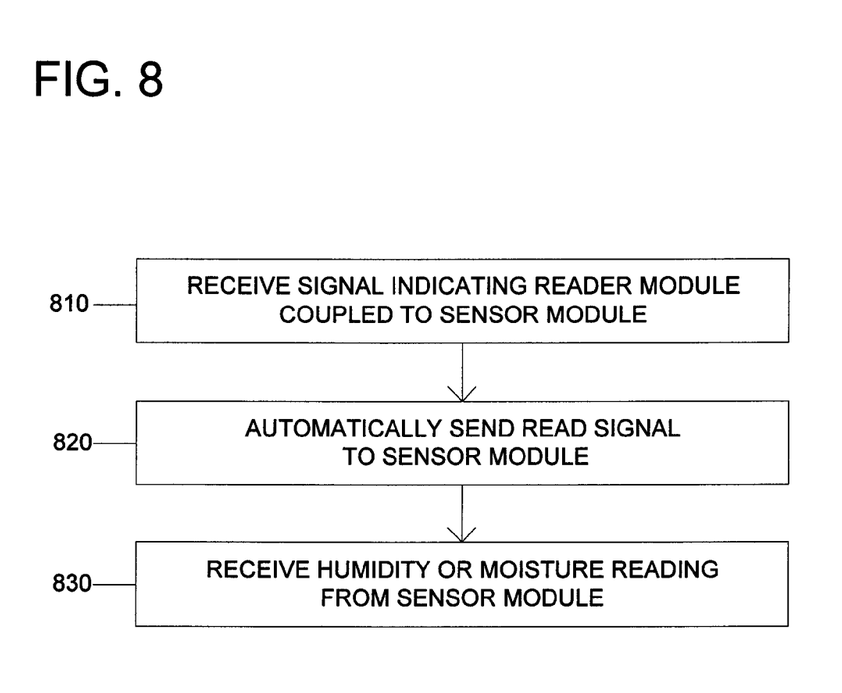
FIGS. 8 and 9 are flow diagrams showing exemplary methods described herein.

FIG. 8 shows an exemplary method of measuring humidity or moisture in a subject material. The method can comprise receiving a signal indicating that the reader module 50 is electrically coupled to the sensor module 30, as shown in block 810. This signal can be received by the controller 60 when the connector pins 66 are in contact with the landing pads 30. In response to the signal, the controller 60 can automatically send a read signal to the sensor module, as shown in block 820. The automatic sending of the read signal to the sensor module can occur immediately or substantially immediately after the electrical coupling occurs between the reader module and the sensor module. The controller can also supply power from reader module 50 to sensor module 20. In response to the read signal, the controller 60 can then receive a humidity or moisture reading from the sensor module, as shown in block 830. This reading from the sensor module can be received immediately or substantially immediately after the read signal is sent.

Figure 9:
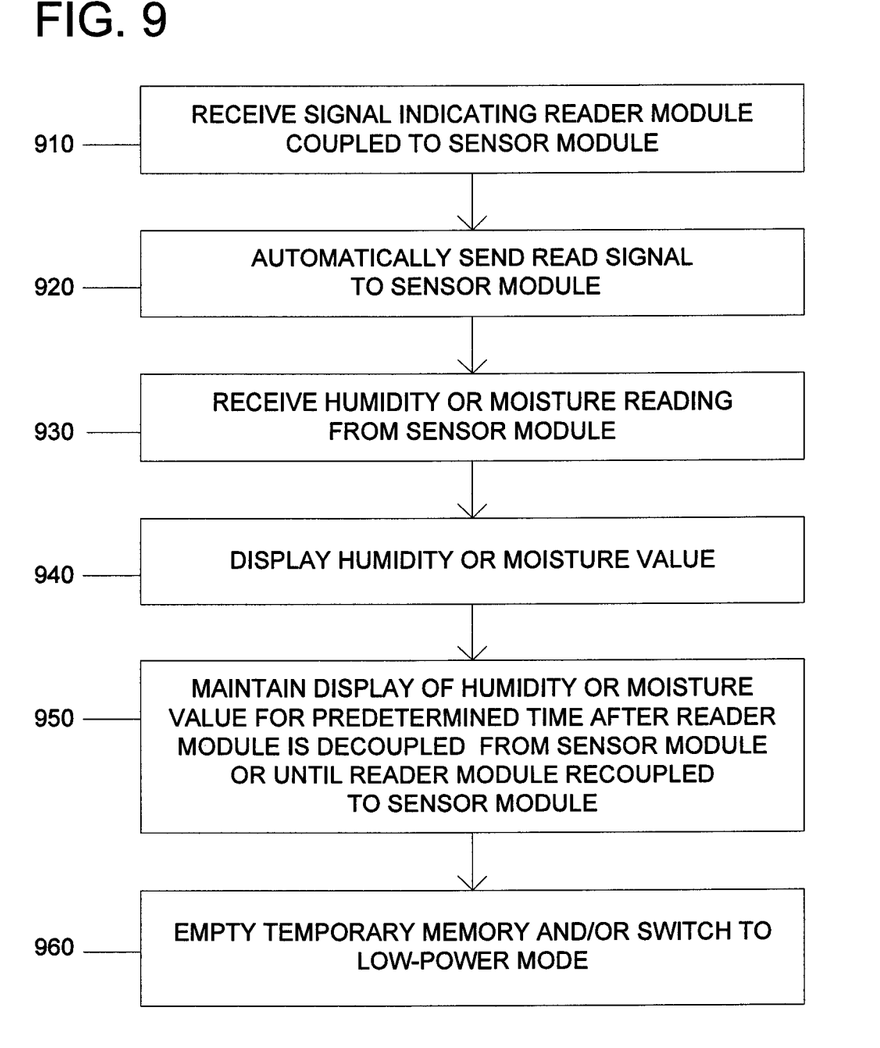

FIG. 9 shows another exemplary method of measuring humidity or moisture in a subject material. Blocks 910, 920 and 930 correspond to blocks 810, 820 and 830 in FIG. 8. After the humidity or moisture reading is received from the sensor module at block 930, a humidity or moisture value, such as RH, corresponding to the humidity or moisture reading can be displayed on the display 64, as shown at block 940. From a user's perspective, the reading can appear on the display 64 in a very short time, such as less than one second, after the user inserts the reader module into contact with the sensor module. After the humidity or moisture value is initially displayed at block 940, this display of the humidity or moisture value can be maintained for a predetermined period of time after the reader module is decoupled from the sensor module or until the reader module is recoupled to the sensor module, as shown in block 950. After this predetermined period of time, the controller can lose its temporary memory and/or switch to a low-power mode or off, as shown in block 960. The process can then be repeated to take another measurement. In this way, a user can insert the reader module in any orientation and immediately remove the reader module and recover the sleeve once the reading is displayed. The reading then remains displayed so that the user can read/record it after removing the reader module.

Figure 10:
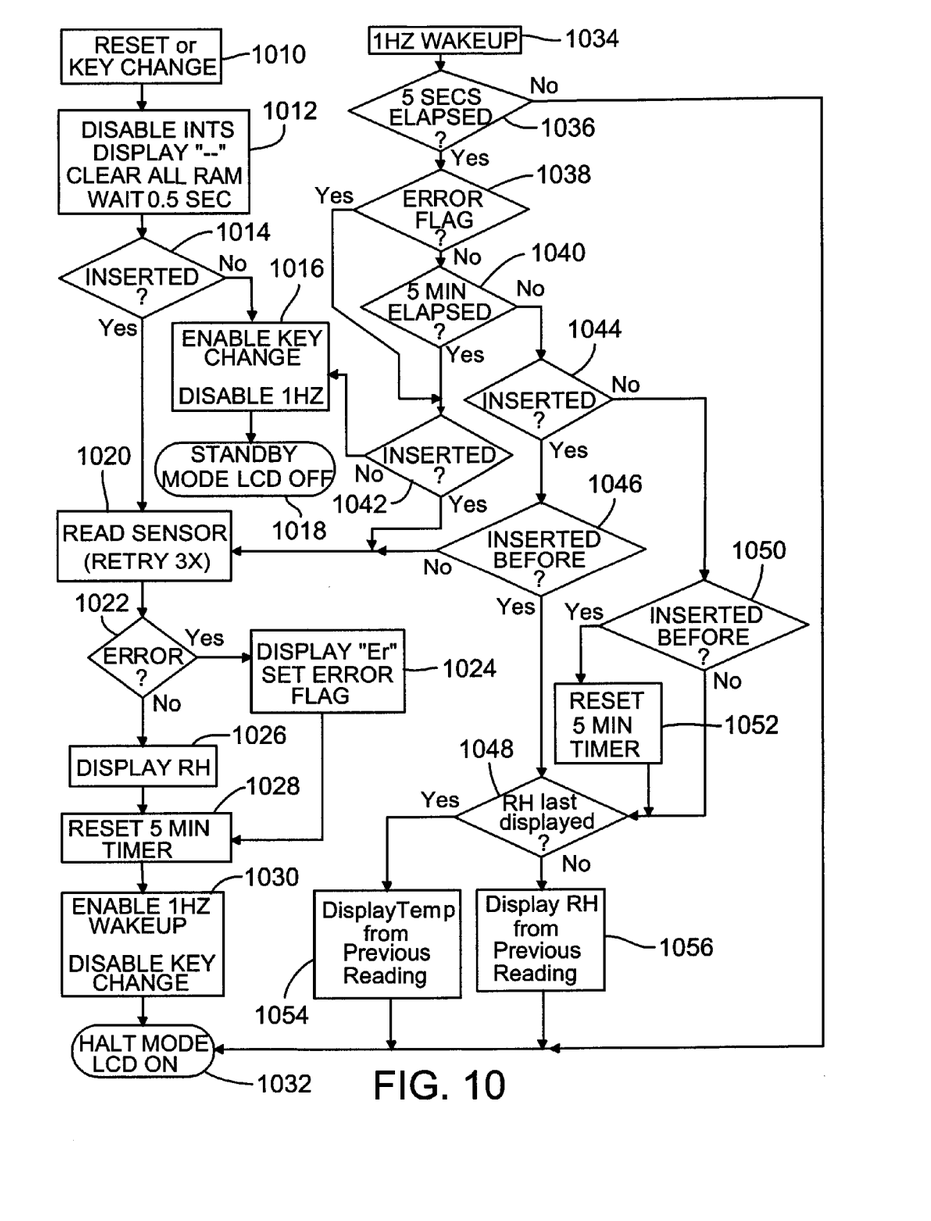
FIG. 10 shows an exemplary algorithm that can be employed by embodiments described herein.

FIG. 10 shows an exemplary algorithm that can be used to measure humidity in concrete using the devices described herein. The algorithm elements shown in FIG. 10 and described below are only examples, and one of ordinary skill will understand that many other related algorithms are possible by adding, removing and/or modifying one or more of the algorithm elements. Each of these related algorithms is included in the scope of this disclosure, though they are not specifically described.

When the center pin 70 and the first pin pair 72 make contact with the central pad 32, the center pin 70 can become electrically coupled to the first pin pair 72, causing an interrupt signal to the controller 60. The interrupt signal can cause a key change in the controller 60, as shown in block 1010. In some embodiments, the key change can cause the controller 60 to automatically switch from the low-power mode to the active mode. In addition to the interrupt signal, the controller 60 can be configured to receive an equivalent signal from a manual "reset" button (not shown) on the reader module 50, as is also shown in block 1010. In such embodiments, a user can press the reset button to manually cause the controller 60 to begin the reading process and/or switch to the active mode.

After the key change or a reset, the controller can disable its interrupts, clear its memory (e.g. RAM), and/or cause the display 64 to display an indication, such as "-", that measurement is about to begin or is occurring, as shown in block 1012.

When all of the pins 66 are connected to the respective pads 30, the controller 60 can determine that the reader module 50 has been completely electrically coupled to the sensor module 20, as shown in block 1014. Because this complete connection can occur a short time after the center pin 70 and the first pin pair 72 make contact with the central pad 32, the controller can be configured to delay a short time, such as about 0.5 seconds, after detecting the interrupt signal before attempting to read the sensor 22, as shown in block 1012. If the reader module 50 is not inserted, the controller can enable the key change, as shown in block 1016, and switch to the standby or low-power mode, as shown in block 1018, such that the process can begin anew with the next reset or key change. Temporary memory can be lost when the controller enters the standby mode.

The controller 60 can then send a read signal and/or supply power to the sensor 22 and begin reading the sensor, as shown in block 1020. The time between the interrupt signal and reading the sensor 22 can be less than a second, minimizing the amount of heat that can be transferred between the reader module and the sensor module. The controller can retry reading the sensor a set number of times, such as 3 times, to get a reading. If a reading cannot be made, an error can be detected at block 1022 and an indication, such as "Er", can be displayed and an error flag set, as shown in block 1024. Otherwise, the controller can determine the RH and temperature of the subject material from the sensor, store the values in temporary memory, and begin displaying the RH and/or the temperature on the display, as shown in block 1026.

In some embodiments, a timer can be set once the RH is displayed, as shown in block 1028. The timer can be set for a predetermined period of time, such as five minutes, after which time the display can be turned off and the controller can switch to the low-power mode. This time period can give a user sufficient time to record the RH value being displayed. After the timer begins, the controller can begin periodically and repeatedly reassessing the situation, such every 1 second, as shown in block 1030. For example, at each assessment, the controller can check to see how much of the timer period has elapsed and check if the reader module 50 is still connected with the sensor module 20. During this periodic assessment phase, or halt mode, the display can be continuously displaying an RH value and/or a temperature value, as shown in block 1032, and the controller can awake every one second to reassess, as shown in block 1034.

In some embodiments, if less than a predetermine delay period, such as five seconds, has elapsed since the timer was set, as shown in block 1036, the controller can stop the current assessment and wait another second to perform the next assessment. This delay period can prevent the device from inadvertently taking multiple readings within a short time. After the delay period, the controller can check if RH measurement was successful or if an error flag was set, as shown in block 1038. If an error flag was set, the controller can check if the reader module is currently inserted (electrically connected with the sensor module), as shown in block 1042. If inserted, the begin attempting to read the sensor again at block 1020. If not inserted, the controller can enable key change and go into standby mode, as shown in blocks 1016 and 1017, waiting for an interrupt signal to restart to process. With this feature, if an error occurred in the reading of the sensor, the user does not have to wait the whole five minutes before the trying again or before the device goes into standby mode.

If no error is detected at block 1038, then the controller can check if the timer period has expired, as shown in block 1040. If the timer period has elapsed, the process can continue to block 1042 as described above. If the timer period has not elapsed, the controller can check if the reader module is inserted at block 1044. If the timer period has not elapsed and the reader module is still inserted, the controller can check whether or not the reader module was inserted the last time it checked (e.g., one second ago), as shown in block 1046. If the reader module was not inserted before but is inserted now, then the controller can begin attempting to read the sensor again, at block 1020. Thus, if the user takes a reading, removes the reader module, then reinserts the reader module (after the delay period), the user can start taking new readings without having to wait the full timer period.

If the reader module is currently inserted and was previously inserted, then the RH value and/or temperature value can remain displayed, as shown at blocks 1048, 1054 and 1056. This would be the case if the reader module has been left in the sleeve after the reading was taken. A similar result can occur if the reader module is currently not inserted (at block 1044). In that case, the controller checks if the reader module was inserter that last time it checked, at block 1050. If not, then it proceeds to display RH or temperature at block 1048 without resetting the timer. If the reader module is currently not inserted but was inserted the last time the controller checked (i.e., the reader module was just removed), the timer can be reset, as shown in block 1052, and then the display pattern can proceed at block 1048, giving the user a full timer period after removal to read and record the measurements.

At block 1048, the controller can check if RH was displayed the last time the controller performed an assessment. If so, then the display can be switched to show temperature for a predetermined period of time, such as five seconds. After that time period, the display can be switched back to RH for a time period. This toggling pattern can continue, alternatingly displaying RH and temperature, until timer period expires at block 1040, the reader module is reinserted at block 1046, or the controller is manually reset, turned off, or the batteries are removed.

In an exemplary use, one or more sleeves 2 with sensor modules 20 mounted therein, can be inserted into corresponding number of holes at different locations and/or depths in subject material. A user can use a single reader module 50 to take RH and/or temperature readings from multiple sleeves/ sensor modules. The user can remove the cover 40 from a first sleeve, insert the reader module without regard to rotational orientation, and a reading can automatically be taken with in a second. The user can then remove the reader module and can have timer period (e.g. 5 minutes) to record the RH and/or temperature readings, which can be alternatingly displayed. If an error occurred (e.g., "Er" is being displayed), the user can wait the delay period (e.g., 5 seconds) and the reader module will automatically re-attempt to take measurements. Otherwise, the user can remove the reader module from the first sleeve and reinsert the reader module into a second sleeve to read another sensor module at a different location/depth in the subject material, without having to wait out the timer period. Thus, the user can read and/or record many sensor modules at many different locations all within a short time.

In some embodiments, the reader module 50 can be configured to wirelessly transmit data to an external location, such as to an external storage device. In one example, the controller can determine an RH value from the sensed humidity and temperature data and then wirelessly transmit the determined RH value to an external storage device. The transmission can be made via any wireless means, such as a radio signal, such as Bluetooth™. The receiving storage device can be any known apparatus for receiving and storing wireless data. This wireless transmission of data can be in addition to or alternative to storing the data internally and/or displaying the data on a display, such as an LCD screen.

Regardless of how the data is handled, each RH reading can be more accurate because heat transfer disruptions at the sensor are minimized. Heat transfer can be minimized due to a combination of various advantageous factors, such as: (1) the sensor module remains within the subject material such the sensor is at thermal equilibrium with the subject material when the sleeve cover is removed; (2) the use of polymer materials for the sleeve and housings that have low thermal conductivity; (3) the minimized contact area between the connector pins and the landing pads; (4) the rotation non-specific nature of the electrical connection between the reader and sensor modules; and (5) the automatic touch-and-sense feature, which results in a minimized time delay between inserting the reader module and the measurements being taken.

In view of the many possible embodiments to which the principles of this disclosure may be applied, it should be recognized that illustrated embodiments are only examples and should not be considered a limitation on the scope of the disclosure. Rather, the scope of the disclosure is defined by the following claims. We therefore claim all that comes within the scope of these claims.

I claim:

1. An apparatus for measuring humidity or moisture, comprising:
    a sensor module comprising a humidity or moisture sensor in electrical communication with a first set of terminals; and
    a hand-held reader module comprising a controller in electrical communication with a second set of terminals that are mateable with the first set of terminals such that the hand-held reader module is electrically connectable to and electrically disconnectable from the sensor module, the hand-held reader module being configured to read humidity or moisture data from the sensor in response to making electrical connection with the sensor module;
    wherein the first set of terminals comprises plural connector pins and the second set of terminals comprise plural landing pads, and wherein the plural connector pins and the plural landing pads make a same electrical connection regardless of the rotational orientation of the hand-held reader relative to the sensor module; and
    wherein the landing pads include multiple concentric rings, and the connector pins include multiple redundant pin pairs, such that each of the redundant pin pairs makes electrical contact with one of the concentric rings, wherein each of the redundant pin pairs includes two pins that are electrically coupled together and to the controller.

2. The apparatus of claim 1, wherein the hand-held reader module, upon reading the sensor, is configured to display a humidity or moisture value on a display for a predetermined period of time after the hand-held reader module is electrically disconnected from the sensor module or until the reader module is reconnected to the sensor module.

3. The apparatus of claim 1, wherein the controller comprises an active mode and a low-power mode, and the controller is configured to automatically switch from the low-power mode to the active mode in response to making electrical connection with the sensor module.

4. The apparatus of claim 1, wherein the hand-held reader module is configured to transmit information based on the humidity or moisture data to an external storage device.

5. The apparatus of claim 1, wherein the hand-held reader module, in response to making electrical connection with the sensor module, supplies power to the sensor module to activate the sensor.

6. The apparatus of claim 1, wherein the controller has an interrupt line coupled to a first of the connector pins, and a power or ground source coupled to at least a second of the connector pins, the apparatus configured such that when the hand-held reader module is electrically connected to the sensor module, the first connector pin is electrically connected to the second connector pin to create an interrupt signal to the controller and cause the controller to read the sensor.

7. The apparatus of claim 1, further including a sleeve into which the sensor module is mountable, wherein the reader module includes an elongated outer casing with the first set of terminals at one end thereof and a display at an opposite end thereof.

8. An apparatus for measuring humidity or moisture, comprising:
   a sensor module comprising a humidity or moisture sensor in electrical communication with a first set of terminals; and
   a hand-held reader module comprising a controller in electrical communication with a second set of terminals that are mateable with the first set of terminals such that the hand-held reader module is electrically connectable to and electrically disconnectable from the sensor module, the hand-held reader module being configured to read humidity or moisture data from the sensor in response to making electrical connection with the sensor module;
   wherein the first set of terminals comprises plural connector pins and the second set of terminals comprises plural landing pads, and wherein the controller has an interrupt line coupled to a first of the connector pins, and the controller has a power or ground source coupled to at least a second of the connector pins, the apparatus configured such that when the hand-held reader module is electrically connected to the sensor module, the first connector pin is electrically connected to the second connector pin to create an interrupt signal to the controller and cause the controller to read the sensor.

9. The apparatus of claim 8, wherein the hand-held reader module, upon reading the sensor, is configured to display a humidity or moisture value on a display for a predetermined period of time after the hand-held reader module is electrically disconnected from the sensor module or until the reader module is reconnected to the sensor module.

10. The apparatus of claim 8, wherein the controller comprises an active mode and a low-power mode, and the controller is configured to automatically switch from the low-power mode to the active mode in response to making electrical connection with the sensor module.

11. The apparatus of claim 8, wherein the plural connector pins and the plural landing pads make an equivalent electrical connection regardless of the rotational orientation of the hand-held reader relative to the sensor module.

12. The apparatus of claim 8, wherein the hand-held reader module is configured to transmit information based on the humidity or moisture data to an external storage device.

13. The apparatus of claim 8, wherein the hand-held reader module, in response to making electrical connection with the sensor module, supplies power to the sensor module to activate the sensor.

14. The apparatus of claim 8, further including a sleeve into which the sensor module is mountable, wherein the reader module includes an elongated outer casing with the first set of terminals at one end thereof and a display at an opposite end thereof.

15. An apparatus for measuring humidity or moisture, comprising:
   a sensor module comprising a humidity or moisture sensor in electrical communication with a first set of terminals; and
   a reader module comprising a controller in electrical communication with a second set of terminals that are mateable with the first set of terminals such that the reader module is electrically connectable to and electrically disconnectable from the sensor module, the reader module being configured to read humidity or moisture data from the sensor in response to making electrical connection with the sensor module;
   wherein the first set of terminals comprises plural connector pins and the second set of terminals comprise plural landing pads, and wherein the plural connector pins and the plural landing pads make an equivalent electrical connection regardless of the rotational orientation of the reader module relative to the sensor module; and
   wherein the landing pads include a plurality of rings, and the connector pins include a plurality of redundant pin pairs, such that each of the redundant pin pairs makes electrical contact with one of the plurality of rings, and wherein each of the redundant pin pairs includes two pins that are electrically coupled together and to the controller.

16. The apparatus of claim 15, wherein the reader module, upon reading the sensor, is configured to display a humidity or moisture value on a display for a predetermined period of time after the reader module is electrically disconnected from the sensor module or until the reader module is reconnected to the sensor module.

17. The apparatus of claim 15, wherein the controller comprises an active mode and a low-power mode, and the controller is configured to automatically switch from the low-power mode to the active mode in response to making electrical connection with the sensor module.

18. The apparatus of claim 15, wherein the reader module, in response to making electrical connection with the sensor module, supplies power to the sensor module to activate the sensor.

19. The apparatus of claim 15, wherein the controller has an interrupt line coupled to a first of the connector pins, and a power or ground source coupled to at least a second of the connector pins, the apparatus configured such that when the reader module is electrically connected to the sensor module, the first connector pin is electrically connected to the second connector pin to create an interrupt signal to the controller and cause the controller to read the sensor.

20. The apparatus of claim 15, further including a sleeve into which the sensor module is mountable, wherein the reader module includes an elongated outer casing with the first set of terminals at one end thereof and a display at an opposite end thereof.

\* \* \* \* \*